United States Patent
Godsmark et al.

(10) Patent No.: US 7,880,046 B2
(45) Date of Patent: Feb. 1, 2011

(54) LOW CORROSION IN ZEOLITE OLIGOMERISATION

(75) Inventors: John S. Godsmark, Grez Doiceau (BE); Georges M. K. Mathys, Bierbeek (BE); Hubertus J. Beckers, Keerbergen (BE); Raphael F. Caers, Edegem (BE); Roger Eijkhoudt, GC Breda (NL); Stephen H. Brown, Bernardsville, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 329 days.

(21) Appl. No.: 11/914,643

(22) PCT Filed: Jun. 16, 2006

(86) PCT No.: PCT/EP2006/005852
§ 371 (c)(1),
(2), (4) Date: Jun. 2, 2008

(87) PCT Pub. No.: WO2006/133967
PCT Pub. Date: Dec. 21, 2006

(65) Prior Publication Data
US 2008/0312484 A1    Dec. 18, 2008

(30) Foreign Application Priority Data
Jun. 17, 2005  (GB) ................. 0512377.3

(51) Int. Cl.
*C07C 2/02*  (2006.01)
(52) U.S. Cl. .............. 585/518; 585/502; 585/520; 585/530; 585/532; 585/533
(58) Field of Classification Search .............. 585/503, 585/518, 530, 532, 533, 502, 520
See application file for complete search history.

(56) References Cited

U.S. PATENT DOCUMENTS 2,694,686 A  * 11/1954  Reeves et al. ............... 502/214

(Continued)

FOREIGN PATENT DOCUMENTS

WO    WO 03/082778    10/2003

(Continued)

OTHER PUBLICATIONS

Perry, et al., "Process Control" in Perry's Chemical Engineer's Handbook, R. H. Perry and D. W. Green, ed., McGraw-Hill, 7th ed., 1997.*

(Continued)

*Primary Examiner*—Glenn A Caldarola
*Assistant Examiner*—Bradley Etherton
(74) *Attorney, Agent, or Firm*—Andrew B. Griffis; Leandro Arechederra

(57) ABSTRACT

Water reacts on molecular sieve catalysts used in oligomerization reactions and forms oxygenated compounds, in particular organic acids that may cause corrosion problems downstream of the reactor, in particular in distillation tower overhead systems and downstream thereof. A lowering of the presence of water in the feed prior to contacting thereof with the molecular sieve brings a significant reduction in corrosion downstream. At the same time, it has a significant beneficial effect on catalyst activity and brings a significant extension of catalyst life. Lowering water in the feed is particularly effective when organic nitrogen-containing Lewis bases are present in the feed, even at low levels.

23 Claims, 1 Drawing Sheet

U.S. PATENT DOCUMENTS

| | | | | |
|---|---|---|---|---|
| 4,153,638 A | * | 5/1979 | Bercik et al. | 585/526 |
| 4,440,509 A | * | 4/1984 | Agarwal | 374/166 |
| 4,456,779 A | | 6/1984 | Owen et al. | |
| 4,487,985 A | | 12/1984 | Tabak | |
| 4,547,602 A | | 10/1985 | Tabak | |
| 4,709,111 A | * | 11/1987 | Ward | 585/503 |
| 4,788,366 A | | 11/1988 | Harandi et al. | |
| 4,939,314 A | * | 7/1990 | Harandi et al. | 585/533 |
| 5,672,800 A | | 9/1997 | Mathys et al. | |
| 6,107,535 A | * | 8/2000 | Rossini et al. | 585/823 |
| 6,111,159 A | * | 8/2000 | Huff et al. | 585/529 |
| 6,550,963 B2 | * | 4/2003 | Daily et al. | 374/179 |
| 6,684,914 B2 | | 2/2004 | Gershman et al. | |

FOREIGN PATENT DOCUMENTS

WO    WO 2004/009518    1/2004

OTHER PUBLICATIONS

Stepanov et al., "Interaction of Acetonitrile with Olefins and Alcohols in Zeolite H-ZSM-5: In Situ Solid-State NMR Characterization of the Reaction Products," Chemistry—A European Journal, 1997, vol. 3, Issue No. 1, pp. 47-56.

NPRA, "ExxonMobil Olefins to Gasoline: EMOGAS Technology for Catpoly Units," Annual Meeting, Mar. 13-15, 2005, San Francisco, CA.

* cited by examiner ion and oligomerisation reactions of such cracked products.

LOW CORROSION IN ZEOLITE OLIGOMERISATION

CROSS REFERENCE TO RELATED PATENT APPLICATIONS

This application is a national stage filing of International Patent Cooperation Treaty Application No. PCT/EP2006/005852 filed Jun. 16, 2006, which claims priority from Great Britain Application 0512377.3 filed Jun. 17, 2005, the disclosure of which is fully incorporated herein by reference.

FIELD OF THE INVENTION

The present invention relates to improvements in or relating to the oligomerisation of olefins over a molecular sieve catalyst, more particularly a zeolite catalyst, and which are affected by even small amounts of water as well as by certain nitrogen containing components brought in by their feedstocks.

BACKGROUND OF THE INVENTION

The condensation reaction of an olefin or a mixture of olefins over an acid catalyst to form higher molecular weight products is a widely used commercial process. This type of condensation reaction is referred to herein as an oligomerisation reaction, and the products are low molecular weight oligomers which are formed by the condensation of up to 12, typically 2, 3 or 4, but up to 5, 6, 7, or even 8 olefin molecules with each other. As used herein, the term 'oligomerisation' is used to refer to a process for the formation of oligomers and/or polymers. Low molecular weight olefins (such as propene, 2-methylpropene, 1-butene and 2-butenes, pentenes and hexenes) can be converted by oligomerisation to a product which is comprised of oligomers and which is of value as a high-octane gasoline blending stock and as a starting material for the production of chemical intermediates and end-products. Such chemical intermediates and end-products include alcohols, acids, detergents and esters such as plasticiser esters and synthetic lubricants.

Industrial oligomerisation reactions employing molecular sieve catalysts are generally performed in a plurality of tubular or chamber reactors, similar to those processes employing solid phosphoric acid (SPA) catalysts. With SPA catalysts, the pressure drop over the catalyst bed or beds is increasing gradually over the duration of the run, due to coking and/or swelling of the catalyst pellets, and the reactor run is typically terminated when a maximum allowable pressure drop over the reactor is reached. Molecular sieve catalysts do not show pressure drop increases similar to SPA catalysts. Oligomerisation reactors using molecular sieve catalysts are therefore characterised by longer reactor run lengths, and are typically decommissioned when the catalyst activity has dropped to an unacceptably low level. With these catalysts, the reactor run length that can be achieved is therefore much more sensitive to compounds or impurities in the feed that affect the catalyst activity or deactivate the catalyst, such as catalyst poisons. Strong bases, such as the proton bases or Bronsted bases, are known poisons for the molecular sieve oligomerisation catalysts, which are acidic. Such bases in hydrocarbon streams are often nitrogen containing compounds, such as amines and amides, and they are typically removed from feedstocks for oligomerisation reactions, including those using molecular sieve catalysts. Such organic nitrogen-containing Bronsted bases are characterised by at least one hydrogen atom bound to the nitrogen atom, and are known proton acceptors. Other organic nitrogen components do not have any hydrogen atom bound to the nitrogen, and its nitrogen atom may have three bonds to 1, 2 or 3 surrounding carbon atoms. These nitrogen atoms however still have a free electron pair, and therefore can still act as a base, termed a Lewis base. Lewis bases are known to be much weaker bases as compared to Bronsted bases, and therefore are often ignored or not considered poisons to acid catalysed processes.

Industrial hydrocarbon conversion processes employing molecular sieve catalysts typically run for several weeks before a catalyst change is required or a decommissioning of the reactor is needed. In industrial processes the feeds for the reactions are generally streams derived from catalytic or steam cracking, which may have been subjected to fractionation. The nature of such refining activities is such that there will be variations in the composition of the feed. In addition it may be desired to change the nature of the feed during a reactor run. The catalyst activity and the reaction conditions vary according to the composition of the feed. Furthermore, the reactions are exothermic and the exotherm also depends upon the nature and amount of olefin present in the feed. Isobutylene and propylene are particularly reactive generating a large exotherm.

The feeds that are used for olefin oligomerisation are typically obtained from petroleum refining or petrochemical operations. In particular they are obtained from either the steam cracking or catalytic cracking of streams obtained from the processing of crude oil. The compositions of these oligomerisation feeds depends upon the feed to the cracking process and the cracking conditions that are employed. The composition of the oligomerisation feed and particularly the amount and nature of the impurities in the feed can have a significant impact on the conversion and selectivity of the oligomerisation reaction and can also effect the useful lifetime of the catalyst. Alternatively the feeds may be produced by the conversion of oxygenates such as methanol to olefins.

It is well known that certain impurities such as sulphur containing contaminants and basic nitrogen containing species have an adverse effect on the useful lifetime of the catalyst and processes are employed to remove these contaminants from the feeds.

The present invention is concerned with such processes that employ a molecular sieve, e.g. zeolite oligomerisation catalyst and is particularly concerned with the provision of conditions which enhance the overall conversion and selectivity of the reaction and extend catalyst life. Olefin oligomerisation may be performed in tubular or chamber reactors although the present invention is particularly useful in reactions performed in tubular reactors.

Throughout this application conversion is the percentage of fresh olefin feed that has reacted (and hence not retrieved anymore in the stream(s) leaving the process). It may be determined by making a material balance over the reactor/process and calculating % conversion as 100×(In−Out)/In.

Selectivity is typically defined as the production of the selected desired product(s). On (primarily) C4 feed these are typically the octene molecules, although the dodecenes may be included, and on (primarily) C3 feed these are the hexenes and dodecenes but even more importantly the nonene molecules. On mixed C4/C5 feeds these are the octenes and nonenes (and optionally the decenes), and on mixed C3/C4 feeds these are the hexenes, heptenes, octenes, nonenes (and optionally the decenes). Undesired typically are the heavier oligomers (typically the C10 or C11+ molecules except for the tetramer (mainly C12) made from propylene), and the molecules that are not directly made by oligomerisation of fresh feed olefins, but made via a mechanism involving cracking to other than those fresh feed olefins. On C4 feeds those are typically everything but the octenes. On C3 feed it is other than C6/9/12s. Selectivity is expressed as a % wt found of the desired material relative to the amount of reaction products (excluding unreacted olefins and paraffins).

Throughout an extended production run, the reaction temperature is generally increased to maintain the desired level of conversion and the reaction is typically terminated when a certain temperature representing the limits of the apparatus is required for the desired level of conversion. Catalyst life is expressed as the amount (weight) of oligomer made per amount (weight) of catalyst and provides a value that compensates for throughput variations, and is a result from a material balance over the process throughout the run. The highest temperature that can be tolerated depends upon the equipment and the feed employed, although we prefer to terminate at 300° C. or less to avoid oligomer cracking reactions.

Tubular oligomerisation reactors employing zeolite catalysts typically comprise one or more bundles of tubes also termed "reactor tubes", mounted, preferably vertically, within a shell. The tubes are packed with the zeolite catalyst typically in the form of pellets and the feed containing olefin reactant is passed through the tubes in which it is oligomerised, typically from top to bottom. The length of the tube in industrial practice is generally from 2 to 15 meters, often from 3 to 14 meters, preferably from 5 to 12 meters, more preferably from 6 to 11 meters, yet more preferably from 8 to 10 meters. The diameter of the tube, the thickness of the walls of the tubes and the materials from which the tubes are made are important, since oligomerisation reactions are exothermic and it is important to dissipate the heat generated by the oligomerisation reaction. Accordingly relatively small diameter, such as an external or outer diameter (OD) from 25 to 75 mm, tubes are preferred, more preferably 35 to 50 mm diameter (OD) tubes. The reactor tubes are preferably of high strength material and are thin walled and of a material with a high thermal conductivity. The high strength is required to withstand the high pressures that are generally used in the oligomerisation of olefins in a tubular reactor employing a zeolite catalyst. Duplex stainless steel is a preferred material for manufacture of the tubes. Higher strength steel and smaller tube diameters allow for smaller wall thicknesses. Duplex stainless steel and a 50.8 mm (2 inch) OD tube allow the wall thickness to be as little as 3 to 4 mm, leaving an internal diameter of the tube of 35-45 mm.

Any convenient number of tubes may be employed in a tubular reactor shell. Typically, operators use from 25 to 500 tubes per shell, arrayed in parallel. Preferred reactors contain about 77 tubes or 180 tubes per shell, although any number may be employed to suit the needs of the operator, e.g. 360 or 420. The tubes are preferably mounted within the shell and a temperature control fluid is provided around the outside of the tubes but within the shell to dissipate heat generated by the exothermic reaction that, in use, takes place within the reactor tubes. One reactor may comprise multiple bundles of tubes, for example up to 7 or 8, or even 9 bundles, and preferably, in use, the temperature of the fluid within the tubes in all the bundles in the same reactor is controlled by means of the same temperature control fluid system. Hot oil or boiling water, under pressure to control the temperature, may be used as the temperature control fluid.

The present invention may also be applied to oligomerisation reactions performed in adiabatic or chamber type reactors. These typically employ a plurality of adiabatic reaction zones in series, with a means of temperature control between the individual reaction zones. In one embodiment, these reaction zones are separate reactors that each contain at least one catalyst bed, and temperature control may then conveniently be accomplished using heat exchangers between the reactors. As an alternative, a chamber reactor may be employed, where several catalyst beds may be provided within one reactor vessel. Temperature control in chamber reactors is more conveniently provided by interbed quench, whereby a fluid that is cooler than the process fluid is injected into the reactor and mixed with the warmer process fluid between two beds. In this way the inlet temperature to the next bed may be controlled by controlling the flow of the quench fluid. The quench fluid typically contains primarily inert components, but may still contain minor amounts of reactants. A most convenient quench fluid in an oligomerisation process is the mixture of unreacted olefins and paraffins that is left over after the reaction, and which is separated from the oligomer product in the stabiliser tower, which is typically but not necessarily the first distillation tower located downstream of the reaction zone. This liquid is available as a cool liquid from the stabiliser overhead condenser and accumulator system. Part of this mixture is typically purged from the process to control the amount of paraffins and other light inerts in the reaction system. Another portion of this stream may be used as diluent for the fresh feed going to the reactor. And a third portion may thus be used for interbed quench, to control the temperature at the inlet of each catalyst bed, the temperature rise over the catalyst bed, and indirectly therefore also the temperature at the outlet of each catalyst bed. Alternatively or in addition, other cool fluids of less reactive composition may be employed as reactor quench, such as selected portions of the oligomer product although that may be less desired.

Historically, oligomerisation reactions over acid catalysts are performed in the presence of water. The light olefinic feedstreams from refinery operations that are used for olefin oligomerisation typically contain water vapour from upstream in the process, because it is either added such as in steamcracking or catalytic cracking, or formed such as in the process of converting oxygenates to olefins. The feedstreams are therefore typically at their water dew point when they are condensed. This water will typically condense together with the light hydrocarbons, and there is usually sufficient water present to form free water that is then separated off by gravity. The liquid hydrocarbon stream containing the olefinic feed for oligomerisation is immiscible with water and has a lower density. It will tend to form a separate liquid layer above any liquid water phase. Due to some water solubility, this layer will contain dissolved water. If a free water phase is formed, the level of dissolved water will be up to the solubility limit of water in the hydrocarbon stream. This limit is different for different hydrocarbon components, and therefore depends on the composition of the hydrocarbon stream.

U.S. Pat. No. 5,672,800 (WO 93/16020) is concerned with the oligomerisation of olefins employing a zeolite catalyst, particularly the zeolite ZSM-22. U.S. Pat. No. 5,672,800 does not indicate the nature of the reactor that was used although it employs small quantities of materials and indicates that under the conditions employed in U.S. Pat. No. 5,672,800 conversion and catalyst life can be improved if the oligomerisation is performed in the presence of water. The compositions in the examples show a significant improvement in catalyst life when water is present. The catalyst life achieved on propylene using the techniques of U.S. Pat. No. 5,672,800 is 1240 weight of oligomer per unit weight of catalyst and 2500 weight of feed per unit weight of catalyst.

The ExxonMobil Olefins to Gasoline (EMOGAS) process was described at the Annual Meeting of the National Petrochemical and Refiners Association, 13 to 15 Mar. 2005, at the Hilton Hotel, San Francisco, Calif., USA. The paper described olefin oligomerisation in a tubular reactor employing a zeolite catalyst and specified that the reaction temperature is controlled with water that is fed on the shell side of the reactor. It is stated that the heat released due to EMOGAS reactions in the tubes evaporates water on the shell side. The temperature profile in the tubular reactor is said to be close to isothermal and the temperature is controlled via the shell side water pressure, which controls the temperature of evaporation, and also by the reactor feed temperature. The tubular reactors are said to usually operate at a pressure between 5.5 and 7.6 MPa (800 and 1100 psi) and temperatures around 204° C. (400° F.).

The EMOGAS brochure also shows Chamber-type reactors using interbed quench for temperature control. Adiabatic reactors in series for oligomerisation using interbed/interreactor cooling for temperature control are discussed in U.S. Pat. Nos. 4,487,985 or 4,788,366 which are silent about water in the feed, but discuss refinery streams as suitable feedstocks that typically are saturated with water. U.S. Pat. No. 4,547,602 discusses such reactors for its second stage (FIG. 3 and column 6), an oligomerisation feed stream that is saturated with water at the temperature of separation (typically a few 100 ppm wt). U.S. Pat. No. 4,456,779 Table I shows a material balance for an oligomerisation process using 3 adiabatic reactors in series, with interreactor cooling. The fresh feed olefins (which are produced by fluid catalytic cracking see column 11, line 33), the oligomerisation reactor feed and its effluent are all shown with a water content of 0.01% mole, i.e. 100 ppm molar.

It has been standard practice to hydrate the feed to oligomerisation reactors in order to prevent excessive temperatures being generated particularly at the start of a reaction run when the feed contacts fresh catalyst and the exotherm is at its highest. As stated previously U.S. Pat. No. 5,672,800 relates to the hydration of olefin feeds to oligomerisation to control temperature and reduce the exotherm. According to U.S. Pat. No. 5,672,800, if the feed has a water content of from 0.05 to 0.25% molar preferably at least 0.06% molar based on the hydrocarbon content of the feedstock, the yields of the desired higher molecular alkene oligomers can be increased and the zeolite catalyst becomes deactivated more slowly. U.S. Pat. No. 5,672,800 specifies that, if the water content is below 0.05 molar %, it should be increased. In Example 1 of U.S. Pat. No. 5,672,800 the moisture content of a feed having an initial water content of 0.02 molar % is hydrated to give a water content of 0.15 molar % and the catalyst life is increased significantly as is the propene conversion. U.S. Pat. No. 6,684,914 also hydrates the olefin feed to at least 0.05 mole % water. International Publication Number WO 2004/009518 suggests that the minimum water content of the hydrated olefin feed should be 0.005 wt %.

Although the use of water has been found to be beneficial, we have found that the water can interact with the zeolite to form oxygenates from the hydrocarbons in the feed. Although the reaction is not fully understood it is believed that some of the olefins in the feed and the water react over the catalyst to form alcohols and ketones which can be converted to acids which have been found to cause severe corrosion in the overhead system of the stabiliser column and associated recycle equipment, which requires equipment replacement and associated down time, and/or the selection of corrosion resistant construction materials. A zeolite catalysed oligomerisation plant is typically equipped with an upstream process step, assuring there is enough water in the feed to the reactor to suit the needs of the catalyst. This is typically in the form of, or combined with, the water wash to remove basic nitrogen compounds from the feeds, and the water wash step is therefore preferentially done using a slightly acidic water stream. Water presence has been known to be beneficial in zeolite-based oligomerisation to control reactivity and typically a minimum level of water in the reactor feed has been proposed.

Water may also be introduced into the feeds during further treating processes, such as for the removal of sulphur. Sulphur removal from such light hydrocarbon streams is typically done by washing with an aqueous solution of an amine, such as mono-ethyl-amine (MEA) or with aqueous caustic soda. Such sulphur removal steps are typically followed by water washing. The wash water is optionally kept slightly acidic, a method which is sometimes used to remove polar and basic nitrogen compounds which can be poisonous for the oligomerisation catalyst, and this also introduces water.

However it has now been found that the presence of water in the oligomerisation reaction on molecular sieve catalysts in both tubular and chamber reactors may lead to the formation of light molecular weight oxygenate compounds, amongst which there are organic acids, which can corrode equipment.

Following the oligomerisation in a tubular or a chamber reactor the product is typically passed to a stabiliser separator which is sometimes known as a drum or tower where the product is separated into the desired oligomer and the unreacted material and reaction byproducts.

The stabiliser is usually a distillation tower in which the desired oligomer is recovered as the bottoms product, while the unreacted material is taken off overhead. Any water—and oxygenates with low carbon number present in the reactor product—will move up the tower with the vapour, and mostly condense in the tower overhead condenser, together with most if not all of the hydrocarbon lights, such as the unreacted olefins and alkanes. With partial condensers, there typically remains a—much smaller—vapour stream that is not condensed but disposed of as vapour, typically by letting it down into the site fuel system to recover its heating value. The condensing of water with low carbon number oxygenates, in particular the acids, has been found to create corrosion problems in the overhead system of the stabiliser tower.

Part of the condensed hydrocarbon lights are pumped into the stabiliser tower to provide reflux in the tower and the rest is either purged from the system (e.g. routed to the LPG pool or sold as it is as LPG, i.e. "Liquified Petroleum Gas") or partly used as a diluent recycle to the oligomerisation unit. The recycle may be returned to the feed in order to control olefin strength of the stream going to the reactor. In chamber plants parts of this recycle may be used as interbed quench for temperature control of the reaction in the individual reactor beds. The presence of the oxygenates and acids in the recycle streams can cause corrosion problems in the recycle systems and in the systems receiving the stabiliser overhead streams.

The reaction effluent (after typically some cooling and reduction of pressure) may flow into a splitter tower first, which optionally is preceded by a flash drum, although typically both the vapour and the liquid from the flash drum flow into the splitter tower albeit usually at different levels in the tower. The splitter tower overhead stream then passes to the stabiliser, and the stabiliser bottom stream then only contains part of the polymer, i.e. the lighter oligomers. Some of the lighter oligomers, such as hexenes and heptenes may be recovered from the stabiliser tower bottoms by further fractionation in a "light product" unit, and the remaining stream containing heavier oligomers may be routed for further recovery to a "heavier product unit". The splitter tower bottom stream may contain very little of the lighter oligomers and it may be taken to a "rerun tower" where the very heavy oligomer is retained in the bottom. The "intermediate" oligomers taken overhead may be combined with the heavies from the light product unit for recovery of octenes, nonenes, decenes, undecenes and/or dodecenes by further fractionation in the "heavier product unit".

Reference in this specification to removal of heat from the (reactor) tubes of tubular reactors or temperature control of the (reactor) tubes is, in context, intended to mean removal of heat from the materials contained within the tubes where reaction takes place (generally comprising, in use, unreacted feed, reaction products and catalyst). It will be appreciated that the heat generation on the catalyst and heat removal from the tube wall may cause a radial temperature gradient through the cross-section of the tube, such that the centre of the tube may become significantly hotter than the wall of the tube. The larger the tube diameter, the larger this temperature gradient may be. One convenient way to remove the heat from the tubes and carry out the temperature control is to provide boiling water to generate steam within the reactor on the shell side around the exterior of the tubes. This provides a good heat transfer coefficient on the shell side. If the present invention is performed in a chemical plant or a refinery, the steam generated by the oligomerisation process may be readily integrated into the steam system typically present at such sites. The reaction heat from oligomerisation may then be put to use in another part of the oligomerisation process, or with another process in the plant or the refinery, where heat input is required.

In adiabatic type reactors, the highest temperatures occur at the outlet of the reactor beds. These temperatures may be controlled by controlling the inlet temperature to the corresponding reactor bed, either by interbed cooling or by interbed quench, and by reactor inlet temperature control for the first bed.

On an industrial scale it is desirable that oligomerisation reactors can run continuously for as long as possible (i.e. long catalyst life) and that the conversion and selectivity of the reaction is maintained over such extended production runs.

As already indicated, the oligomerisation of olefins over zeolite catalyst is a highly exothermic reaction, particularly the oligomerisation of propylene and/or isobutylene. The high temperatures generated by the exotherm can lead to carbonaceous deposits on the catalyst caused by a build up of condensed, heavy hydrocarbons similar to asphalt. Such deposits are commonly termed "coke" and, may occur inside the zeolite or molecular sieve pores and/or on the outer surface. This coke formation can lead to deactivation of the zeolite catalyst. In general, the higher the concentration of olefin in the feed, the higher will be the rate of heat release from the catalysed reaction, and hence the higher the temperatures reached. Consequently there will be a higher rate of coke formation. This has placed a limit on the maximum concentration of olefin that can be tolerated in the feed. Since the oligomerisation reaction is highly exothermic it is necessary to control the temperature and in a tubular reactor this is usually accomplished by encompassing a bundle of reactor tubes within a shell through which is passed a temperature control fluid. Conveniently the temperature control fluid is oil (usually hot oil), or preferentially a boiling liquid because of the improved heat transfer on the side of the boiling liquid. This boiling liquid may be an organic stream, preferentially a stream taken from another point in the process and its return stream, usually a mix of vapor and liquid, returned to another suitable point in the process. The reaction heat may as such be used as heat supply to a reboiler of a distillation tower. Most conveniently the liquid is water, at least partially converting to steam in the reactor shell side. The water is conveniently supplied from a steam drum and the boiling temperature can then readily be controlled by varying the pressure in the steam drum. Conveniently the steam drum collects the water/steam return stream from the reactor shell side, and provides the water supplied to the reactor shell side. The steam generated by the reaction heat may be removed from the steam drum and may be put to use elsewhere.

In adiabatic reactors such as chamber reactors, as in tubular reactors, coke buildup on the zeolite catalyst will be highest at the location of the higher temperatures, which in adiabatic reactors occur at the bed outlets. In adiabatic type reactors it is therefore particularly important to control the bed outlet temperatures such as by the use of a quench fluid as mentioned previously. The use of a quench fluid brings the additional benefit over a conventional heat exchanger, in that it tends to dilute the reactants in the process fluid, so that the same amount of reaction heat generated will cause a lower temperature rise of the stream passing through the catalyst bed.

Traditionally water has been provided in the feed as an additional means to control the temperature of the reaction and to compensate for the exotherm.

SUMMARY OF THE INVENTION

We now have surprisingly found that the life of the molecular sieve oligomerisation catalyst can be significantly improved if, contrary to conventional practice and the teachings of U.S. Pat. No. 5,672,800, the water level in the feed is below 30 ppm wt based on the total hydrocarbon level in the feed.

The present invention therefore provides a process for the oligomerisation of olefins comprising feeding an olefin-containing feed stream to a reactor containing a molecular sieve, e.g. zeolite oligomerisation catalyst wherein the olefin-containing feed stream contains less than 30 ppm of water based on the total weight of hydrocarbon.

In a further embodiment the invention provides a process for the oligomerisation of olefins comprising feeding an olefin-containing feed stream to a reactor containing a molecular sieve, e.g. zeolite oligomerisation catalyst wherein the olefin feed is dried to contain less than 30 ppm water based on the total weight of hydrocarbon.

DETAILED DESCRIPTION OF THE INVENTION

Figure 1:
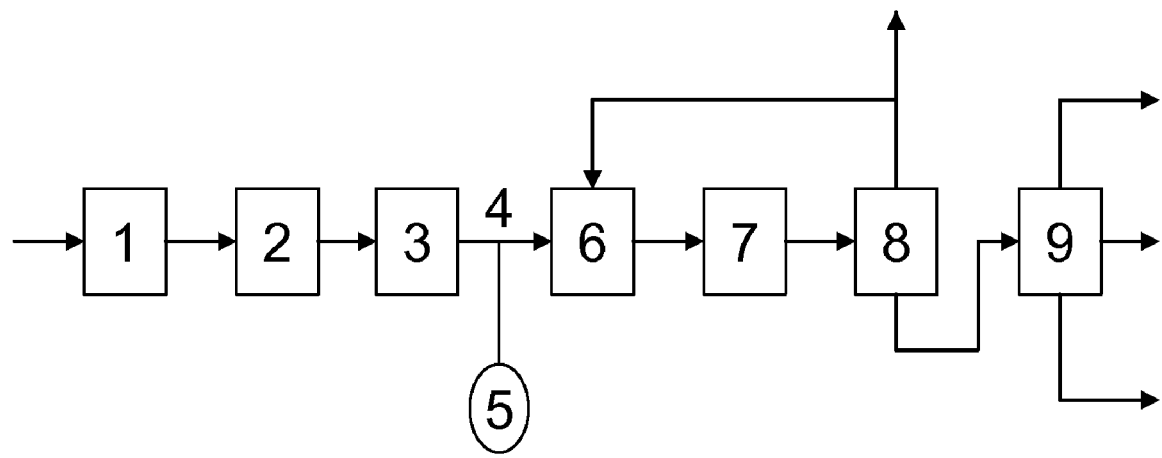
FIG. 1 is a schematic block diagram of an olefin oligomerisation process in one embodiment of the invention.

Both embodiments of the invention are particularly useful when the process is continuous and the product at the outlet of the reactor is fed to a separator in which the oligomer is separated from the unreacted materials and byproducts. In particular when unreacted material is separated overhead and at least partially recycled, we have found that the reduction in the water content of the feed results in a significant reduction in corrosion in the overhead and in the recycle equipment, particularly the recycle pumps.

An additional benefit of the present invention is that we have found that the reduction in the water content of the olefin feed improves catalyst life. In particular the reduction in the water level has been found to improve the life of the catalyst with feeds containing organic nitrogen-containing Lewis bases, e.g. nitriles such as acetonitrile or propionitrile.

Despite this improvement we have further found that catalyst life is further extended if the level of organic nitrogen-containing Lewis bases in the feed is below 5 ppm in combination with a level of water in the feed below 30 ppm. Other organic nitrogen-containing Lewis bases besides nitriles, may be N-methyl-pyrrolidone, morpholines such as N-formyl morpholine, pyridine and quinoline.

Accordingly the present invention further provides a process for the oligomerisation of olefins comprising feeding a hydrocarbon olefin-containing stream to a reactor containing a molecular sieve oligomerisation catalyst wherein the olefin-containing feed contains less than 30 ppm of water and less than 5 ppm of an organic nitrogen-containing Lewis base based on the weight of hydrocarbon in the feed.

In particular the feed contains less than 5 ppm acetonitrile and/or propionitrile. Preferably the level of organic nitrogen-containing Lewis base in the feed is below 3 ppm, more preferably below 2 ppm, even more preferably below 1 ppm by weight.

Techniques for treating hydrocarbon streams for lowering the concentration of organic nitrogen-containing Lewis bases may be found for instance in our copending application U.S. Ser. No. 60/781,623 filed Mar. 10, 2006, which is incorporated herein by reference.

We have also found that organic nitrogen-containing Lewis bases, such as acetonitrile or propionitrile, can be tolerated in olefin-containing hydrocarbon feeds to molecular sieve oligomerisation reactions at concentrations of 0.1 ppm wt or above, preferably 0.2 ppm wt or above, more preferably 0.3 ppm wt or above and most preferably 0.4 ppm by weight or above, based on the total hydrocarbon feed to the molecular sieve oligomerisation catalyst.

The invention therefore also provides for a preferred embodiment of the process wherein the concentration of the organic nitrogen-containing Lewis base in the olefin-containing hydrocarbon stream prior to contacting with the molecular sieve oligomerisation catalyst is not less than 0.1, preferably not less than 0.2, and more preferably not less than 0.3 ppm and most preferably not less than 0.4 ppm by weight, based on the total hydrocarbon feed.

The preferred concentration of said Lewis base in the hydrocarbon feeds being contacted with the molecular sieve oligomerisation catalyst is from 0.1 to 2.0 ppm by weight based on the total hydrocarbon stream, preferably from 0.2 to 1.5 ppm by weight, more preferably from 0.3 to 1.0 ppm by weight, and most preferably from 0.4 to 0.8 ppm by weight.

This embodiment brings the further benefit that the burden of regenerating or discarding the undesired byproducts from the treatment step for reduction of the Lewis base is reduced.

In the case where the Lewis base is a nitrile, the nitrile content of the feed may conveniently be measured by on line gas chromatography, preferably but not necessarily combined with a mass spectrometry, performed on the feed to the reactor. Polar GC columns are preferred because they separate more readily the polar compounds from the sample matrix. By way of example, a GC-MS having a GC-column FFAP (which stands for Free Fatty Acids Phase, and in this case is a nitroterephthalic acid modified polyethylene glycol phase) with dimensions of 50 m×0.32 mm ID and a coating layer having 0.5 μm dry film thickness, has been used to measure nitriles in C3 and/or C4 streams that resemble liquefied petroleum gas (LPG) streams. One method is to program the oven temperature to stay at 60° C. for 10 minutes and then to raise to 220° C. at a rate of 10° C. per minute. The injector temperature may be 200° C., and the injection volume 1 μl via a liquid sampling valve. Further preferred parameters include a split of 1/10, and Helium as the carrier gas, at a constant rate of 1.0 ml/min. The MS-parameters may be for example: Thermo Voyager MS apparatus, Ionization mode EI+ (Electron Impact Plus), Detector voltage 500 V, GC-interface temperature 210° C., acquisition type: Selected Ion Monitoring (SIM), ion mass/charge (m/z)=41. Quantification may be obtained by injecting a liquefied gas (LPG-type) standard with a known amount of acetonitrile as external standard. A detection limit of 0.2 ppm wt for acetonitrile is readily achievable using this technique.

Other methods proposed in literature include a GC-LOWOX analyzer, using a CP-Lowox column of 10 m by 0.53 mm ID and 10 μm film thickness and a CP-Sil 5 CB Ultimetal column of 25 m by 0.53 mm ID and 0.5 μm film thickness. The LOWOX system comprises a switching device that may send part of the sample from one column to the other. The first column (CP-SIL 5CB) is typically non-polar and serves as a stripper column for heavy hydrocarbons, if any would be present. The second column (CP-LowOx) is typically very polar ad serves as the analytical column. The proposed temperature programme is 5 minutes at 50° C., and ramping to 240° C. at a rate of 20° C./minute. The method further uses helium as the carrier gas, an FID detector, an injection volume of 0.2 μl, and direct injection with a liquid sampling valve (LSV), optionally combined with a backflush, depending on the sample nature such as its average carbon number and carbon number distribution. This method may be applicable for a wider range of samples and a wider selection of Lewis bases. It does not require the use of a mass spectrometer and/or an MS-detector, in particular when references of target components are available and the separation is sufficient.

Another suitable analytical technique is by Nitrogen Chemiluminescence GC. Such method may employ a GE Analytical (formally Sievers) Nitrogen Chemiluminescence Detector (NCD) mounted on an Agilent 5890 GC. Organic samples are typically completely combusted in a dual plasma burner. The NO produced may then be sent to an ozonizer that forms excited $NO_2$. The photochemical decomposition of the excited $NO_2$ may then be detected by a wavelength selective photomultiplier tube. The GC column preferably is an RTX-1 of 30 m by 0.32 mm ID with a 1 μm film. The oven temperature programme is preferably isothermal (holding 5 minutes at 60° C.) for $C_3$ and/or $C_4$ containing (LPG-type) samples. The apparatus may be equipped with a 2 μl high pressure liquid sampling valve. The injector temperature preferably is 200° C., helium may be used as the carrier at a total flow of 25.2 ml/min, a split ratio of 10.0/1, a split flow of 20 ml/min and a column flow of 2 ml/min. The NCD conditions are: hydrogen set at 4.0 ml/min, oxygen at 11.9 ml/min, a pressure of 102 mm Hg, and a temperature of 960° C. Quantification may be performed against a standard blend. The achievable detection limit using this technique is readily 0.2-0.3 ppm wt, and lower amounts, in the range of 0.1-0.15 ppm may be seen under low noise conditions.

The present invention is particularly useful when applied to the oligomerisation process described in copending Patent Application GB 0512377.3.

When employed with a tubular reactor the techniques of the present invention can reduce the temperature fluctuations along the length of the reactor tube and improve the control of the temperature along the length of the reactor tube in order to enhance the life of the catalyst and the conversion achieved. When the conversion obtained in the reactor reduces due to catalyst aging and/or coking, the reactor temperature is typically increased to compensate for the reduced catalyst activity. This is conventionally done by raising the pressure on the shell side of the reactor, which increases the temperature at which the heat exchange fluid boils, a technique particularly convenient when the heat exchange fluid is boiling water and steam is generated by the reaction heat. This procedure is called temperature ramping, and is typically limited up to a maximum temperature. This maximum may be imposed by the design pressure and/or temperature of the reactor itself, the reactor shell side, or, if present, the steam drum. The maximum temperature may also be determined by undesired side reactions becoming too prominent above a certain reactor temperature. When that maximum temperature is reached and catalyst activity reduces further, feed flow rate may be reduced in order to maintain olefin conversion. When this control possibility is exhausted, the reactor is considered at the end of its run and it is taken out of service, and the deactivated catalyst may be removed and regenerated. Regeneration may also be performed in situ. The catalyst may be replaced by fresh catalyst or by a different batch of regenerated catalyst. The invention is concerned with the conditions to be used to sustain the activity of any molecular sieve, e.g. zeolite catalyst unlike the EMOGAS paper which specifies a particular catalyst that is more stable.

In the present invention, the water content of the feed stream is preferably monitored continuously employing an on line analyser. We have found that the water content may be determined by GC, we have also found that a Panametrics on line analyser which employs a platinum on aluminium electrochemical probe is particularly useful. If the water content of the feed exceeds 30 ppm then the feed can be dried by any conventional means. In processing of C4 feeds, the feed to the reactor may be the C4 byproduct derived from the production of methyl tertiary butyl ether (MTBE), which removes most of the isobutylene from C4 refinery products by the formation of MTBE. This byproduct can contain dimethyl ether, which needs to be removed, and this removal may be achieved by distillation, and this distillation step can also be used to remove any water in the C4 byproduct stream that is the feed to oligomerisation. Other examples of suitable drying techniques include fractionation, vapor stripping, liquid/liquid extraction using a hydrophylic fluid such as a glycol, and adsorption on a solid such as an adsorbent.

Removal of nitriles and other organic nitrogen-containing Lewis bases from the oligomerisation feed may be performed by a washing step with water, which should be performed upstream of the drying step. Alternatively, organic nitrogen-containing Lewis bases may be removed by adsorption on a selective adsorbent, such as Selexsorb CD-X. Typically, the performance of such adsorbents is negatively affected by the presence of water, meaning that with such adsorbents, the step for removal of organic nitrogen-containing Lewis bases is preferably performed downstream of the drying step.

The present invention is applicable to oligomerisation reactions performed in either chamber reactors or tubular reactors. The invention is however particularly useful for reactions performed in a tubular reactor such as has been previously described. In a chamber reactor the feed passes through a series of beds or chambers containing the zeolite catalyst. It is preferred that the feed passes vertically downwards through the reactor. Typical for a chamber reactor is that the outlet stream of a catalyst bed is quenched by mixing it with a colder stream before the mixture enters the next catalyst bed. The quench stream is typically used to control the temperature of the next catalyst bed. Good mixing of the quench stream with the stream leaving the previous bed is important. The quench stream conventionally is a return stream from downstream in the process, typically containing a lower concentration of reactants than the fresh feed and/or the reactor feed.

The highest bed outlet temperature in an adiabatic type reactor system may be considered the reactor peak temperature. At the startup of a chamber reactor, when all beds are loaded with fresh catalyst, this peak temperature will occur at the outlet of one of the earlier beds, where the reactant concentration is higher than downstream. As the molecular sieve, e.g. zeolite catalyst in this reactor bed deactivates, the temperature rise over the bed will reduce, and this may be compensated by raising the inlet temperature of this bed accordingly. It may also be compensated by letting one of the downstream beds pick up the duty that is lost in the upstream bed. Eventually the catalyst in a reactor bed may loose most or all of its activity, in which case this part of the reaction duty may need to be performed by the catalyst bed or beds downstream. This shift of duty will increase the temperature rise over the downstream bed, and the outlet temperature of this bed may then become the reactor peak temperature.

The composition of material in the reactor varies as the material flows through, usually down, the reactor and begins to react. The olefin will have a lower molecular weight at the beginning (inlet) of the reactor, where it is predominantly unreacted light olefins and it will become progressively heavier towards the reactor outlet as the light olefins are oligomerised to form higher molecular weight olefins. Excessive temperatures caused by the exotherm of the reaction can coke up the catalyst, which leads to deactivation.

In typical operation of the preferred tubular reactor for oligomerisation of olefin feed, with molecular sieve catalyst in the reactor tubes and with a temperature control fluid on the shell side, a temperature profile will be observed over the length of a reactor tube. Conventionally, such operation is performed with the tubular reactor arranged such that the feed inlet is at the top and the reaction product outlet is at the bottom. The following description addresses such an arrangement, but it will be understood that the description applies equally to reactors not in top to bottom arrangement. Typically, the temperature profile initially increases at the inlet of the tube, when reaction heat is generated faster than it can be removed by the temperature control fluid around the tube. As the reactants convert further as they move along the tube and their concentration reduces, the reaction rate reduces and the rate of heat generation reduces. At the same time the temperature in the tube increases, and the heat removal rate through the tube wall increases. The temperature profile then typically goes through a maximum, and then shows a decline further along (down) the tube towards the outlet. As the reaction temperature declines along the tube, also heat removal rate reduces, and the temperature profile may then flatten out before the end of the catalyst bed in the tubes is reached.

In the known tubular processes employing fresh zeolite catalyst, the temperature increase at the initial part (e.g. top) of the tube is sharp, and the temperature profile shows a sharp peak. The fresh catalyst at the initial part (top) of the tube performs most of the reaction. Coke will build up where the temperature is at its highest, which will deactivate the catalyst in that part of the tube. U.S. Pat. No. 5,672,800 seeks to overcome this problem by the addition of water to quench the initial activity of the catalyst. Without this quench the reaction rate will then reduce due to the catalyst deactivation, and hence the rate of heat generation will reduce, and hence the slope of the temperature increase in that part of the temperature profile declines. The catalyst further along (down) the tube will then see a higher concentration of unreacted reactants, and the reaction rate—and hence heat generation rate— will increase in that part of the tube. In this way the peak in the temperature profile, known as "the peak temperature", will move along (down) the tube. In order to compensate for the reduced overall catalyst activity, heat removal is typically reduced by increasing the temperature of the temperature control fluid around the tube. The average temperature in the reactor and the temperature at the outlet of the tube or reactor will thereby be increased as the run progresses. In addition, the temperature of the feed delivered to the tube inlet may be adapted as well. Typically it may be increased to keep as much of the reaction as possible at as early (high) as possible a location in the catalyst bed inside the tube. The peak in the temperature profile therefore may not only move along (down) the tube as a production run proceeds but it may also become less sharp and less pronounced.

The rate of heat generation increases with higher reactant concentration. The peak in the temperature profile is therefore sharper and more pronounced when the olefin concentration in the feed to the reactor is higher. The rate of heat generation is also higher with more reactive reactants, typically with the lighter olefins such as propylene and butenes such as isobutylene. The peak in the temperature profile is therefore also sharper and more pronounced when a higher portion of the available butenes is isobutylene, or when a higher proportion of the olefins fed to the reactor is propylene. In case dienes or acetylenes are present, these are even more reactive and will increase the rate of heat generation, in particular in the upstream part of the zeolite catalyst bed. The total heat of the reaction also depends on the product produced. The greater the degree of oligomerisation of any particular olefin, the higher the heat of reaction, because more monomer molecules will have combined to form the product.

We have found that the techniques of the present invention enable the peak temperature to be reduced and in some instances to be eliminated. This is particularly the situation when the techniques are employed together with the techniques described in our copending Patent Application GB 0512377.3. This application GB 0512377.3 is concerned with the control of temperature and pressure within the reactor tube to within certain limits whereby extended production runs with high conversion of olefin to oligomer may be achieved using the conventional zeolite oligomerisation catalysts with feeds containing higher levels of olefin. According to the present invention, the extended runs may be achieved without the need for the presence of water. In this way the corrosion of the reactor and/or in other parts of the process, in particular the stabiliser overhead system, and recycle equipment can be reduced.

We have found that, regardless of what the overall, average or outlet temperatures of the reactor may be, if the peak temperature is allowed to reach too high a level, the catalyst deactivation rate becomes excessive, and the life of the catalyst bed is reduced; and that in order to obtain good catalyst life in an oligomerisation process comprising a tubular reactor containing zeolite catalyst, it is important to control the peak temperature.

The present invention therefore further provides a process for oligomerising an olefin comprising contacting the olefin with a molecular sieve catalyst in a reactor tube of a tubular reactor having a shell that contains a temperature control fluid for removing heat of reaction from the reactor tube, in which process the olefin-containing hydrocarbon feed to the reactor contains at least 42 wt % of olefin and less than 30 ppm of water based on total hydrocarbon in the feed wherein operating conditions are controlled such that the reaction product mixture exiting the reactor is at a pressure of at least 55 barg and wherein the shell side temperature control fluid parameters are controlled such that the peak temperature in the reactor tube is no more than 50° C. above the temperature of the temperature control fluid as said fluid exits the reactor.

In particular we prefer that the peak temperature be controlled to be no more than 40° C., preferably no more than 30° C., particularly preferably no more than 20° C. and most preferably no more than 10° C. above the temperature of the temperature control fluid as the temperature control fluid exits the reactor.

We have found that, the flatter the temperature profile along the length of the tube, the easier it is to employ conditions that enhance catalyst life. We have also found that a flatter temperature profile may be obtained if the throughput of the olefin-containing feed stream is increased and in particular we prefer to employ a throughput of from 1 to 15 w/w/h, preferably from 2 to 12 w/w/h, more preferably from 3 to 9 w/w/h and most preferably from 4 to 8 w/w/h which has been found to improve the heat transfer or the inside of a tubular reactor. In addition we have found that a low per pass conversion such as a conversion of from 50 to 75% coupled with recycle further flattens the temperature profile. We also prefer to use tubes with a length from 2 to 15 meters, preferably from 5 to 10 meters, and with an inside diameter of 6 cms or less, preferably 5 cms or less, more preferably 4 cms or less, the minimum diameter should be 2 cms. Furthermore where several reactors are employed it is preferred to provide separate preheaters for each of the reactors, so that the feed temperature can be adjusted according to the temperature conditions within the specific reactor. The employment of one or more of these conditions together with the low water level of the present invention has been found to result in a significant improvement in catalyst life.

We have found that, providing those conditions are employed, feeds of single olefins and mixtures of olefins can be processed in tubular reactors employing a zeolite catalyst over extended runs, for example up to 250 days continuous operation, without undesirable loss of catalytic activity. We have found that catalyst life in excess of 3000 tonnes of oligomer per tonne of catalyst may be achieved. The maximum concentration of olefin in the reactor feed that can be processed will depend upon the nature of the olefin or mixture of olefins that are to be oligomerised. However, we have found that propylene containing feeds that contain e.g. up to 65 wt % propylene, more typically up to 60 wt % propylene, most typically up to 55 wt % propylene can be employed. Similarly we have found that butene-containing feeds that contain e.g. up to 80 wt % butene such as up to 70 wt % butene, typically up to 65 wt % butene, most typically up to 60 wt % butene can be processed. Similar amounts can be processed when mixed feeds are employed. The minimum amount of olefin in the feed, according to the invention, is preferably 42 wt %. In the case where the feed contains propylene, the more preferred minimum is 44 wt %, yet more preferably 46 wt % and most preferably 48 wt %. In the case where a butenes feed is employed, the more preferred minimum is 46 wt %, yet more preferably 50 wt %, such as at least 55 wt % and most preferably at least 60 wt %. It should be understood that the higher the amount of olefin that is allowed in the feed to the reactor, the higher the productivity becomes of the oligomerisation reactor.

We have found that the employment of conditions according to the present invention that allow control of the peak temperature is important for satisfactory performance of the oligomerisation of olefins, for example C3 to C6 olefins, over a molecular sieve, e.g. zeolite catalyst and, in particular for oligomerisation performed in a tubular reactor. The peak temperature in a tubular reactor may be measured by inserting a multipoint thermocouple in at least one of the reactor tubes.

We prefer to have at least one centralising means, such as a spider-shaped insert, to be used to keep the thermocouple in or near to the radial centre of the tube. It is preferred that the thermocouple can detect the temperature at various locations along a significant portion of the length of the tube, preferably towards the inlet end of the tube. Desirably, temperature is measured over at least the first 50% or above, or possibly at least the first 60% or 70%, or possibly at least 75% or even 80% or even 85% of the length of the tube from the inlet end, and at a plurality of points. For example it is preferred to make measurements at least 5 but preferably from 10 to 20 points, such as 15 points, in a tube that is 3 to 10 meters (approx 10 to 33 feet) in length. The parameters of the temperature control fluid contained within the tubular reactor, for example the temperature, pressure and/or the flow may then be adjusted in response to the temperature measured by the thermocouples in order to maintain the peak temperature in the tube within the desired range according to the temperature control fluid outlet temperature. By appropriate adjustment of the parameters, this enables the process fluid temperature to be maintained at optimum conditions. The peak temperature may be as high as 300° C. but it is preferably maintained below 260° C., more preferably below 250° C., yet more preferably below 240° C. and most preferably below 235° C. Where the reactor consists of a number of parallel tubes, a multitude of those tubes may be provided with a multipoint thermocouple although this is not essential. When the temperature control fluid exits the reactor at about 250° C., the peak temperature is preferably maintained below 300° C., more preferably below 290° C., yet more preferably below 280° C. and most preferably below 275° C. Peak temperatures of above 325° C., preferably above 310° C., more preferably above 300° C. are less advantageous, because of cracking side reactions. So, when the temperature control fluid exits the reactor at about 300° C., the peak temperature is preferably maintained below 325° C., more preferably below 320° C., yet more preferably below 315° C. and most preferably below 310° C.

The temperature of a tubular reactor is conveniently controlled by passing a temperature control fluid around the shell side of the reactor tubes. In a preferred embodiment the tubular reactor consists of several tubes mounted vertically and in parallel and they may be mounted as a bundle or bundles of tubes. It is preferred that the olefin feed be introduced at the top of the tubes such that it passes through the tubes in a downward direction. The tubes are preferably contained within a reactor shell and the temperature control fluid preferably flows vertically upwards within the reactor shell in counter current to the direction of the flow of the olefin feed. Preferably there are baffles provided on the shell side in order to guide the flow of the temperature control fluid. These baffles typically are arranged perpendicular to the reactor tubes. Alternatively arrangements may comprise co-current upflow or co-current downflow. In one embodiment of the invention the temperature control fluid may be an organic fluid such as hot oil. However, in a preferred embodiment the temperature control fluid is water, preferably maintained at pressure in the range of 5 to 85 bar gauge which results in a temperature in the range of 160 to 300° C. The temperature of the water may be controlled by varying the pressure in the stream drum that separates steam from the boiling water, provides the water for boil up on the shell side of the reactor and collects the shell side outlet stream. In this way the peak temperature, wherever it may occur inside the reactor tube, may be controlled to be within the desired difference from the temperature of the temperature control fluid at the reactor outlet. We have also found that, unlike with conventional SPA catalyst, where a minimum temperature of 140° C., preferably 155° C., is to be maintained when the catalyst is in contact with the olefin feed, in order to avoid the formation of phosphate esters which leach out, decompose downstream and cause corrosion, such a minimum is not imposed with zeolite catalysts. The lowest reactor temperature, which is typically the inlet temperature, may therefore be as low as 80° C., 100° C. or 120° C., but for reasons of overall heat management may be preferably maintained at or above 140° C. In preferred operations the lowest temperature in the reactor tube is kept at least at 180° C., more preferably at least at 190° C.

The improvements of the present invention are derived from the use of feeds containing less than 30 ppm water and in a preferred embodiment from effective control of the reactor temperature profile. We have also found that by employing feed delivery conditions with tubular reactors, e.g. an inlet pressure that establishes a minimum reactor outlet pressure of 55 barg, it is believed that these pressure conditions maintain the material in the reactor tubes of the tubular reactor in a single phase which may be a liquid phase or a dense phase. A significant vapour phase and a two phase system such as a vapour/liquid phase system should preferably be avoided and particularly preferably avoided along the entire length of the tube.

In a preferment of the present invention leading to extended runs, the feed material is fed to the reactor under a pressure such that the material exiting from the outlet of the tubular reactor is maintained at a pressure of at least 55 barg, and thereby the inlet pressure will also be greater than 55 barg. Preferably the outlet pressure is in the range 60 to 80 barg and more preferably at least 65 or 70 or 75 barg.

We also prefer to keep the space velocity of the olefin feed relatively high, for example above 1 wt/wt/hour, preferably from 1-15 wt/wt/hour, more preferably from 2-10 wt/wt/hour and most preferably from 3-8 wt/wt/hour. A high space velocity will improve the heat transfer on the inside wall of the reactor tubes. This, in turn improves the heat transfer from within the reactor tube to the outside of the tube i.e. to the shell side.

Deactivation of a zeolite catalyst during its use to catalyse the oligomerisation of olefins is often believed to be a result of the formation of high boiling polymers as by-products. These by-products can remain on the catalyst and undergo further conversion to higher molecular weight polymers, which resemble heavy tars or asphalt and in some cases even have the appearance of coke-like material. These materials can coat the catalyst particles and plug pores in the catalyst, thereby causing catalyst deactivation. Accordingly, the process of this invention is ideally carried out at a pressure which is sufficient to maintain a liquid or supercritical (dense) phase of hydrocarbon in contact with the catalyst. This liquid or supercritical hydrocarbon phase maintains conditions whereby the high molecular weight polymers or tar are more readily washed off the catalyst, thereby prolonging the catalyst life. The liquid or dense phase also is more effective in removing heat away from the active sites on the catalyst, thereby suppressing the formation of higher molecular weight polymers or tar.

In the practice of the process of this invention employing a molecular sieve, e.g. zeolite catalyst, the olefin-containing feedstock containing less than 30 ppm water is contacted with the catalyst at a temperature, pressure and period of time which are effective to result in conversion of at least a portion of the compounds in the feed to the desired oligomer products. For example, the olefin to be oligomerized may be an olefin from 3 to 9 carbon atoms, preferably from 3 to 6 carbon atoms. The contacting will generally be carried out at a temperature in the range from about 125° to about 300° C. It will be appreciated of course, that the optimum temperature will be a function of the specific reactants employed and their concentration in the feed. The contact temperature will typically be increased over the course of a run in order to maintain economically acceptable overall conversion.

The reactor temperature profile may also be controlled by raising the temperature of the feed to the reactor. The temperature may be raised to, for example, 150° C. to 250° C. such as between 160° C. and 190° C. prior to introduction into the reactor, and this may be accomplished by the provision of any suitable heating means. In a preferred embodiment the feed is heated by use of the heat generated in the reactor, such as by the steam, that has been used to control the temperature in the shell side of the reactor, or by the heat contained in the reactor effluent.

When the fresh feed is rich in olefin, the control of conditions within the reactor tube may be effected by running low conversion per pass and recycle of part of the unreacted olefins (mixed with the paraffins of the same carbon number) separated from the reactor product stream. We have found that when the process of the invention is operated at a conversion per pass of the feed olefin from 40 to 80%, then the selectivity to the true oligomer is significantly higher than compared with when conversions per pass are of 90% or above are obtained. The recycle may still allow to achieve overall olefin conversions that are economically acceptable. The recycle ratio (weight of recycle on weight of fresh feed) may be controlled within a wide range e.g. 0.1 to 2.5, preferably 0.2 to 2.0. For example the ratio can be low, such as 0.2 or 0.3, but can also be higher, such as 0.5, 1.0, 1.5 or 2.0. Typically, the recycle ratio will be selected depending on, for example, the fresh feed composition, the availability (or lack thereof) of another suitable diluent, and any limits on the maximum concentration of olefins in the purge stream. This purge stream contains unreacted olefins and in one arrangement typically comprises all or part of the LPG stream coming from the distillation tower that separates the unreacted olefins and paraffins from the rest of the reaction product after the reactor; such tower is usually called the stabiliser and is often in the first position.

The above-described recycle operation permits the reactor to be operated at a relatively low per-pass conversion, but with a high overall conversion. This enables the overall product yield to be maximised. By way of example the per-pass conversion may be as low as 50%, and may be achieved by steam drum pressure reduction (in the case where the temperature control fluid is water).

By fresh feed that is rich in olefin is meant for example, in the case of a propylene feed, a feed containing at least 70 wt %, at least 85 wt %, at least 92 wt % or at least 97 wt % propylene. For a fresh butenes feed that is rich in olefin is meant a feed containing at least 65 wt %, at least 80 wt %, at least 90 wt % or at least 94 wt % butenes. Isobutylene may be present in proportions as low as 1 wt % or 0.5 wt % or less; or alternatively in higher amounts such as up to 18 wt % or up to 22 wt % based on total fresh feed.

Feed to the reactor does not need to be absolute dry, but preferably contains below 20 wt ppm, most preferably below 10 wt ppm, particularly preferably below 5 wt ppm.

The temperature of the feed at the reactor inlet can be adjusted, as can the space velocity, feed concentration and steam drum temperature (in the case where the temperature control fluid is water) as a further means to provide improved control of the temperature profile along the length of the reactor tube. Adjustment of the feed temperature can allow the temperature profile to be smooth over the entire length of the tube. In a preferred operation the feed inlet temperature is raised to a value that is no more than 20° C. below the peak temperature as measured inside the reactor tube. Inlet temperatures can be controlled by independent preheaters, e.g. heated by steam or by reactor effluent.

The temperature along the reactor tube may also be controlled by filling the reactor tube with a more active catalyst in the bottom of the tube (part near the outlet) and a less active catalyst in the upper (inlet) part of the tube. Such an arrangement is disclosed in our co-pending patent application WO 2005/118512.

Multiple reactors may be put in series, with the upstream reactors running with colder steam temperatures than the downstream ones. Similar to LPG recycle, this allows running high space velocities over a reactor while still reaching high overall conversions. Unlike with solid phosphoric acid (SPA), this is particularly easy to arrange with molecular sieve catalysts, because the pressure drop increase that is typical for SPA catalyst is not observed with zeolite catalysts.

Unlike with solid phosphoric acid catalysts, the use of zeolite catalysts provides stable operation and good selectivities at temperatures up to 300° C. Reactor designs allowing such high temperatures also significantly extend the run length before a molecular sieve catalyst must be removed because of unacceptable activity.

The control of the peak temperature to a value that is no more than 50° C. above the temperature of the temperature control fluid as it exits the reactor, according to the invention, has enabled much improved conversion. Such control may be by controlling the parameters of the temperature control fluid passing through the shell side of the reactor, such as temperature and/or pressure and/or flow rate of the fluid. This controls removal of heat from the reactor tube and so by control of such parameters the temperature difference between peak temperature and temperature control fluid is also controlled. The techniques of the present invention are particularly applicable to operations in which the length to diameter ratio of the tube is at least 50, and in particular at least 100, more particularly from 200 to 300.

When employing a series of reactors, such as in a chamber reactor, the temperature of the material is typically controlled by introducing a quench fluid between the reactors or reactor beds and/or by reducing the concentration of unsaturated materials in the feed. We prefer that the temperature rise across a reactor or catalyst bed be no more than 50° C., preferably no more than 30° C. In order to monitor the temperature, and control the quench as required, the temperatures between each bed may be measured by appropriately placed thermocouples, after the bed outlet before the quench injection, and optionally, after the quench injection at the next bed inlet. It is also preferred that, when using a series of beds, the first bed, usually the upper bed, is more shallow than subsequent beds to allow for the higher activity and greater exotherm at the initial stages of the reaction.

In most industrial processes such as those described previously, the refinery feed that is to be used in the hydrocarbon conversion reactions will contain impurities such as polar compounds. These impurities would be detrimental to the hydrocarbon conversion reaction and are frequently removed prior to the reaction, by for instance a water wash. In olefin oligomerisation the feeds are frequently subject to a first alkaline wash to remove acidic polar species, such as thiols or mercaptans, followed by a weakly acidic water wash. The last water wash typically produces a feed stream which is saturated with water at the temperature at which the water wash is performed and, accordingly, the feed will need to be dried for use according to the present invention.

The invention is particularly but not exclusively concerned with processes suitable for the production of C5 to C20 olefins boiling in the range of 30° to 310° C., preferably 30° to 300° C., more preferably 30° to 250° C., from propylene and/or butene and/or amylene feedstocks or their mixtures, though ethylene may be present as well. In particular the invention is concerned with the production of the olefins shown in the following table.

In a tubular reactor, the catalyst is contained in a reactor tube, generally a multiplicity of tubes which are surrounded by a circulating cooling medium. Preferably these tubes will each typically have an internal diameter of from about 25 mm to about 75 mm as previously discussed, although other diameters can also be used.

The reactor may be provided with means that enable the reactor to be depressurised to flash off hydrocarbons from the catalyst. We have found that this treatment on a zeolite catalyst enables recovery of some of the activity lost during the run.

The alkenes that may be oligomerised by the processes of the invention include propene, and linear or branched $C_4$-$C_6$ alkenes, which may be mono-, or di-polyunsaturated. The process is particularly advantageous for the oligomerisation of propene and butenes, especially isobutylene, and may be used for the oligomerisation of a single alkene, or of mixtures of alkenes of the same or of different carbon numbers. Oligomers that may be produced by the process of the present invention are

| Oligomer Products | Distillation Range (° C.) ASTM D1078 | |
|---|---|---|
| | Initial Boiling Point | Dry Point |
| Pentenes | 30 | |
| Hexenes | 35 | 72 |
| Heptenes | 88 | 97 |
| Octenes | 114 | 126 |
| Nonenes | 135 | 143 |
| Decenes | 155 | 160 |
| Undecenes | 167 | 178 |
| Propylene Tetramers Or Dodecenes | 175 | 225 |
| Tridecenes | 204 | 213 |

The level of di- and polyunsaturates in the feed is typically controlled to below a maximum allowable level. Preferably, the feed composition is limited to containing no more than 100 ppm by weight of acetylene and/or no more than 500 ppm of the C3 polyunsaturates, methylacetylene and propadiene or allene, and/or no more than 2500 ppm or more preferably no more than 1000 ppm of butadiene. We have found that cyclopentene generates the same heat of reaction than pentadiene. The reason for these limitations is the high reactivity and extreme coke forming properties of the di- and polyunsaturates. We have found that if it is necessary to use feeds containing relatively high levels of polyunsaturates, production may be sustained if the olefin concentration in the feed is reduced accordingly. This keeps the carbon deposition low, which would otherwise increase due to the heat generated by the reaction of the higher amounts of polyunsaturates present.

The olefin feed to the reactor is generally a mixture of a reactive olefin and an unreactive diluent, which is typically an alkane, preferably having the same carbon number as the olefin. The rate of heat generated by the oligomerisation reaction depends upon the concentration of the olefin in the feed. The higher the concentration of olefin, the more reactive the feed and the greater the heat that is generated. For example in the operation of tubular reactors employing phosphoric acid catalysts to oligomerise propylene containing feeds, it has been found necessary to limit the amount of olefin in the feed. This is because, despite employing cooling systems such as the steam generation mentioned previously, it has not been possible to perform extended continuous runs with feeds containing more than 50 wt % propylene. Typically is has only been possible to employ feeds containing much less than 50 wt % propylene, some processes operating at 40 wt % propylene or less. In chamber reactors, where temperature is controlled by quench injection and no heat is removed by heat transfer, the reactor feeds typically contain even lower concentrations of propylene, such as 30 or 35 wt %.

The feed streams containing the feed olefins such as C3 and C4 olefins are generally steams derived from steam cracking or catalytic cracking and the composition of the stream will depend upon the raw material from which it is produced and the production technology employed. However, propylene refinery steams typically contain up to 75 wt % or even up to 79 wt % propylene, with the balance being predominantly propane. Similarly, butene refinery steams typically contain up to 70 wt % butenes with the balance being predominantly butanes. Butene streams from steam cracking may contain 90 to 95% butenes, sometimes even 96% wt. The reactivity of the olefins in oligomerisations over zeolite catalysts varies according to the nature of the olefin. However it has not been possible to successfully oligomerise C3 to C6 olefins over extended periods of time in tubular reactors employing a zeolite catalyst if the concentration of propylene in the feed exceeds 50 wt % and generally concentrations below 40 wt % have been employed. This has required the expensive addition of diluent to an olefin-containing refinery feed. Typically the diluent may be additional amounts of the alkane found in the refinery feed and/or it may be provided by recycle of the unreacted material derived from the reactor. The need for diluent not only adds to the expense of the operation but it also reduces the volumetric yield of the reaction with associated economic debits.

The olefin feed may be obtained from an oxygenate stream. In this embodiment the olefin feed stream that is oligomerized is predominantly derived from an oxygenate to olefins unit; meaning that at least 50 wt % of the olefin feed, preferably at least 60 wt %, and more preferably at least 70 wt % of the olefin feed, is derived from an oxygenate to olefins unit. Such a feed stream should be low in sulfur, nitrogen and chlorine, to the extent that essentially no pretreatment will be required for removal of such components. In addition, such a feed stream should have a relatively low concentration of paraffins, compared to such sources as olefins from cracked hydrocarbons. However, such a feed stream will generally contain oxygenated hydrocarbon at a level which would likely adversely impact catalytic life of the zeolite oligomerization catalyst. Therefore, removal of such components is likely required. The benefit in using an oxygenate to olefins stream is that lower levels of inert components, such as propane and butane, are present.

The design of a tubular reactor may be improved to reduce the peak temperature. Smaller tube diameters allow easier heat dissipation from the center of the tubes to the tube walls, and provide for more heat exchange surface per unit of catalyst volume. They also allow for more tubes to be fitted in the same size shell.

Also reactor operations may contribute to a reduction of the peak temperature. Operating at lower per pass conversions, typically combined with separating and recycling part of the unreacted molecules from downstream of the process to the reactor feed, also flattens the temperature profile in the reactor. This is easier when the fresh feed to the oligomerisation process contains less inerts such as alkanes, because a high overall olefin conversion may still be obtainable for the lower per pass conversion, while the olefin concentration in the reactor feed is still conveniently high so that a high reactor volume efficiency is obtained. The alternative is to add reactor volume in parallel, which means additional investment costs.

It is believed that use of the feed which is dry or has a low water level enables the reactor to operate at a lower temperature than has been used with previous systems. In particular the lower temperature may be used at start up of a reaction run. The ability to use a lower temperature at start up contributes to the longer catalyst life because in commercial operations the reaction is allowed to continue until the temperature rises to a certain level when the reaction is stopped as above this temperature cracking, severe coke formation and in catalyst deactivation occurs. Typically the end of run temperature is between 260° C. to 300° C., preferably 270° C. to 290° C.

In the embodiment of the invention concerned with the presence of organic nitrogen-containing Lewis bases such as nitriles in the feed, the reduction in the water level may reduce or eliminate the hydrolysis of the organic nitrogen-containing Lewis bases which produces catalyst contaminants. Accordingly the reduction in the water level can improve catalyst life when processing feeds containing organic nitrogen-containing Lewis bases. However we have also found that the catalyst life may be further increased if the level of organic nitrogen-containing Lewis bases itself is reduced to below 5 ppm. This embodiment is particularly useful when the olefin feed is derived by catalytic cracking since these feeds can have a higher nitrile content. It now has been found that nitriles may also occur in olefin feeds produced by steamcracking, in particular when the steamcracker is converting crude oil feeds derived from crude oil containing organic nitrogen compounds. In addition, the streams generated by steamcracking may be further treated. Some of these treatment steps may also introduce organic nitrogen-containing Lewis base into the hydrocarbon stream that is fed to the oligomerisation process. For example, butadiene concentration may be lowered in steamcracking crude $C_4$ streams, using extraction or extractive distillation employing solvents such as dimethylformamide (DMF), N,N-dimethyl acetamide, β-methoxy propionitrile or N-methyl-pyrrolidone (NMP), or solutions thereof. With an upstream process step that employs such organic nitrogen-containing Lewis base as a process component, the concentrations of said Lewis base in the olefin-containing hydrocarbon stream to oligomerisation may be as high as 50, 100 or upon excursions even 300 ppm by weight, based on the total hydrocarbon stream.

Where the olefin feed stream is obtained by contacting oxygenate with a molecular sieve catalyst, the oxygenate comprises at least one organic compound which contains at least one oxygen atom, such as aliphatic alcohols, ethers, carbonyl compounds (aldehydes, ketones, carboxylic acids, carbonates, esters and the like). When the oxygenate is an alcohol, the alcohol includes an aliphatic moiety having from 1 to 10 carbon atoms, more preferably from 1 to 4 carbon atoms. Representative alcohols include but are not necessarily limited to lower straight and branched chain aliphatic alcohols and their unsaturated counterparts. Examples of suitable oxygenate compounds include, but are not limited to: methanol; ethanol; n-propanol; isopropanol; C4-C20 alcohols; methyl ethyl ether; dimethyl ether; diethyl ether; di-isopropyl ether; formaldehyde; dimethyl carbonate; dimethyl ketone; acetic acid; and mixtures thereof. Preferred oxygenate compounds are methanol, dimethyl ether, or a mixture thereof.

A molecular sieve catalyst is used in the oxygenate to olefin reaction. Such a molecular sieve is defined as any molecular sieve capable of converting an oxygenate to an olefin compound. Examples of these molecular sieves include zeolites as well as non-zeolites, and are of the large, medium or small pore type. Small pore molecular sieves are preferred in one embodiment of this invention, however. As defined herein, small pore molecular sieves have a pore size of less than about 5.0 Angstroms. Generally, suitable catalysts have a pore size ranging from about 3.5 to about 5.0 angstroms, preferably from about 4.0 to about 5.0 Angstroms, and most preferably from about 4.3 to about 5.0 Angstroms.

Suitable molecular sieves are described in International Publication Number WO 2004/009518.

The molecular sieve catalyst used in the present invention may be any molecular sieve that is active in alkene oligomerisation reactions. For example, there may be used a catalyst selected from the group consisting of zeolites of the TON structure type (for example, H-ZSM-22, H-ISI-1, H-Theta-1, H-Nu-10, KZ-2) or zeolites of the MTT structure type (for example H-ZSM-23, KZ-1) or zeolites of the MFI structure type (for example, H-ZSM-5) or zeolites of the MEL structure type (for example, H-ZSM-11) or zeolites of the MTW structure type (for example, H-ZSM-12), or zeolites with the EUO structure type (for example, EU-1), or zeolites H-ZSM-57 02H-ZSM-98, or any member of the ferrierite structure family. Other examples of suitable catalysts are offretites, H-ZSM-4, H-ZSM-18 or zeolite Beta. Reference is made to 'Synthesis of High-Silica Aluminosilicate Zeolites' by P. A. Jacobs and J. A. Martens (published as volume 33 in the series 'Studies in Surface Science and Catalysis') for a review of the synthesis and properties of the aforementioned zeolites.

Additionally, the catalyst can be a zeolite synthesised without addition of a template, for example, faujasites, zeolite L, mordenites, erionites and chabazites, the structures of which are contained in the 'Atlas of Zeolite Structure Types' by C. Baerlocher, W. M. Meler and D. H. Olson (published by Elsevier on behalf of the Structure Commission of the International Zeolite Association, 5th Revision Edition, 2001). Zeolite catalysts having crystal structures that are essentially the same as the crystal structures of the above-mentioned zeolite catalysts, but differing slightly therefrom in chemical composition, may also be used. Examples include zeolite catalysts obtained by removal of a number of aluminium ions from, or by steaming of, the above-mentioned zeolites catalysts; and zeolite catalysts obtained by the addition of different elements (for example boron, iron and gallium), for example, by impregnation or cation exchange, or by incorporation during the zeolite synthesis.

Another type of molecular sieve suitable for the process of the invention is SAPO-11, which has unidimensional 10-rings like ZSM-22 and ZSM-23.

Mixtures of two or more zeolites e.g. a mixture of ZSM-22 and ZSM-57 or ZSM-22 and ZSM-5 can be used as disclosed in EP 0746538 B1. Or alternatively, upon the surface of each zeolite crystal, a layer of another zeolite can be deposited as disclosed in EP 0808298 B1.

The zeolite conveniently has a crystallite size up to 5 μm, such as within the range of from 0.05 to 5 μm, for example from 0.05 to 2.0 μm, and typically from 0.1 to 1 μm. An as-synthesized zeolite is advantageously converted to its acid form, for example by acid treatment, e.g. by HCl, or by ammonium ion exchange, and subsequently calcined before use in the process of invention. The calcined materials may be post-treated, such as by steaming. It is also possible to use, as is known in the art, a material in which silicon and aluminium have been replaced in whole or in part by other elements. Silicon may, for example, be replaced by germanium and/or phosphorus; and aluminium more especially by boron, gallium, chromium or iron. Materials containing such replacement lattice elements are also generally termed zeolites, and the term is used in this broader sense in this specification. The zeolites might be supported or unsupported, for example in the powder form, or used as an extrudate with an appropriate binder. Where a binder is employed, the binder is conveniently a metal oxide, such as alumina or silica and is present in an amount such that the oligomerisation catalyst contains for example from 1 to 99 wt % of the zeolite, more preferably from 50 to 70 wt %.

We prefer to apply vacuum to the oligomerisation reactor shortly after it is taken out of service. We have found that this removes residual hydrocarbons, preventing the build up of even heavier hydrocarbons and permitting easier removal of the catalyst. It has also been found beneficial to include such a flash-off or vacuum treatment in the procedures following an emergency or standby shutdown of the reactor, as it removes a significant portion of still reactive hydrocarbons from the catalyst. It therefore reduces coke build up by preventing condensation reactions on the catalyst. We have found that with this procedure, the catalyst in the reactor typically will retain or gain activity, compared to pre-shutdown, when it is subsequently put into service again after the emergency or standby shutdown.

Selected streams can also be recycled to the reactor to effect dilution or to modify the product slate. For instance, in a propylene fed reactor, C6, C9 or C12 olefin streams, fractionated downstream of the reactors, can be recycled to the reactor to modify the product slate distribution. For example, recycling hexenes may increase nonene selectivity, and recycling nonenes may increase propylene tetramer selectivity. Byproduct streams of carbon numbers other than the above, such as C7-8 or C10-11 mixtures, can also be recycled to reduce their production, if possible even recycled to their full extinction. The feed to the reactors may also be diluted with such recycle streams. These recycle streams may be introduced in order to achieve one or more effects, e.g. to affect phase behaviour in the reactor, to improve catalyst life, to control conversion, to control the selectivity towards particular products, and to assist in control of the exotherm and therefore also the peak temperature.

A problem that may occur with tubular reactors is that the circulation flow of the shell side temperature control fluid is not sufficiently high. In the case of water and steam, this means that there is a high rate of vaporisation within the reactor on the shell side, such that much of the volume in the upper side of the reactor shell side and in the return line to the steam drum is occupied by steam vapour instead of by boiling water. This may impair the heat transfer in the upper part of the reactor tube or bundle of tubes, which makes the temperature profile inside the tube sharper and more difficult to control within the range required according to the invention. When colder boiler feed water is introduced in the steam drum below the liquid level, the temperature of the water flowing from the steam drum to the reactor shell side may become subcooled to below its boiling temperature, which also impairs heat transfer at the lower end of the tube bundle because the heat exchange is not immediately in the boiling regime. We have found that this problem may be alleviated by the solution suggested in our copending Patent Application Number PCT/US06/06014 filed 21 Feb. 2006.

An alternative way to control the temperature profile along a reactor tube, is to have the shell side temperature control fluid flow in co-current mode with the process fluid which can provide the temperature control fluid at its lowest temperature close to the position where the process fluid is at its highest temperature. This may be achieved by forcing the circulation of the water from the steamdrum from top to bottom on the shell side in the case where the reactor tubes are arrayed vertically with their inlets at the top. This creates a risk of vapor pockets on the shell side, but this may be alleviated by providing vent tubes returning to the steam drum. It may alternatively be accomplished by having the process fluid moving upwards inside the reactor tubes while the temperature control fluid flows from bottom to top, for example by forced flow or simply driven by thermosyphon.

In the practice of the invention, when starting up the process in chamber reactors, the fixed bed of zeolite catalyst within the reactor may be initially immersed in a start-up fluid. This typically comprises a less reactive or inert hydrocarbon liquid, such liquid preferably being circulated through the reactor to provide heat to the catalyst bed. The desired conditions of temperature and pressure are then established in the fixed bed of zeolite catalyst. A minimum temperature may also be required before start-up, to minimize or eliminate certain side reactions that could occur with reactive feed on insufficiently heated catalyst. A flow of the feedstock is then introduced over the catalyst bed under the conversion conditions that were previously established when the catalyst was immersed in the start-up fluid.

However, the use of a circulating start-up fluid is not essential as within tubular reactor the heat up of the catalyst bed can be accomplished via the temperature control fluid on the shell side of the reactor. When the desired temperature is reached, normal feed may be introduced into the reactor.

The start-up feed comprises an olefin, optionally a diluent. The relative proportions of the materials in this feed depend upon the nature of the olefin and the oligomerisation conditions. The reactions are strongly exothermic and accordingly a diluent such as a paraffinic or a heavy olefinic hydrocarbon is generally used. For example when the feed for a tubular reactor consists of C3 olefins, we prefer that the feed contain from 40 or 42% to 60% or 65%, or 80% or 90% or 95% e.g. 48 to 52% by weight of olefins, with the balance being a paraffinic or a heavy olefinic hydrocarbon diluent, such as a C3-C5 refinery paraffinic stream. Such feeds may be readily available as that which may be obtained from a catalytic cracker. Its olefin content may be reduced if needed by recycling of unreacted paraffins or low olefinic streams found elsewhere or recovered from the reactor effluent. If butene is to be oligomerised in tubular reactors we prefer to use a feed containing up to 80%, more preferably up to 70% or up to 60% olefins, e.g. from 50% to 70% olefins. Feeds containing lower amounts of olefin are generally employed in chamber reactors.

The materials obtained from the process of the present invention will generally be a mixture of desired olefin oligomers, unreacted olefins, diluent (if any is used), water and other impurities. The materials are therefore separated, generally by fractional distillation primarily into the olefin oligomers, the unreacted olefins and, if present, the diluent. The unreacted olefins and diluents may be recycled to the oligomerisation reactor. The olefin oligomers may then be purified as required for use in subsequent reactions. For example the oligomers may contain trace amounts of sulphur which may damage a hydroformylation catalyst. Accordingly, if the olefins are to be used as a feed for hydroformylation, the feed may need to be desulphurised. Similarly the olefin oligomers may contain trace amounts of chlorine which may also be detrimental to hydroformylation catalysts and may need to be removed. If the hydroformylation catalyst is not damaged by sulphur or chlorine, the catalyst in the subsequent hydrogenation step to produce the alcohol derivatives may be damaged by these compounds, and hence sulphur and chlorine are preferably removed, most preferably to very low levels. Furthermore the olefin oligomers themselves are frequently mixtures of oligomers of different carbon number. For example oligomerisation of a mixture of propylene, butene and amylene can result in a mixture of C6 to C13 oligomers and this mixture can then be separated by fractional distillation to obtain the oligomer or oligomer mixtures desired for a particular purpose.

The process of this invention can be used in connection with the conversion of a mixture of C3 and C4 olefins to gasoline blending stock by oligomerisation. In such an embodiment, the feed will be comprised of at least about 25% by weight of olefins. A typical olefin-containing feedstock to a polymerisation unit for conversion to oligomers in the gasoline boiling range will comprise a mixture of propane, butane, 2-methylpropane, propene, 1-butene, 2-butene and 2-methylpropene, wherein the olefin concentration is in the range from about 35 to about 60% wt. Ethylene and ethane may also be present, albeit typically in minor amounts. However it will be appreciated that the olefin-containing feedstock can have a variety of other compositions which include but are not limited to, other olefins or olefin mixtures, other diluents and the presence of a minor amount of aromatic compounds. In addition olefin concentrations can be used which are outside this range.

In a further embodiment the present invention is used for the oligomerisation of olefins such as ethylene, propylene, butenes and amylenes to produce C6 to C13 olefins which can be used as feeds for hydroformylation reactions for the production of aldehydes and alcohols. The aldehydes may then be oxidised to produce acids or hydrogenated to produce alcohols. The alcohols may then be used in the production of synthetic esters such as plasticiser esters or synthetic lubricants or in the production of surfactants. The olefins may be hydroformylated using low pressure rhodium catalysed hydroformylation technology or high pressure hydroformylation technology which is typically cobalt catalysed, but rhodium is also used. The present invention is particularly useful in the production of feedstocks which are hydroformylated in the manner described in WO 2005/058787. Where the aldehydes produced by this method are hydrogenated, this may readily be accomplished by the method described in WO 2005/058782. The aldehydes may be oxidized to the corresponding carboxylic acids. Both the acids and the alcohols may be esterified to esters. These esters may be plasticizer esters for PVC, such as phthalates, adipates or trimellitates, or they may be lubricant esters or lubricant additive esters such as polyol esters. A suitable esterification process is described in WO 2005/021482 or our copending application PCT/EP2006/005068, filed 24 May 2006. The oligomers may also be hydrogenated to alkanes, which may be used as low sulphur, low aromatic, low pour point hydrocarbon fluids suitable in end uses such as solvents and thinners in paints, printing inks, as stove fuels, or as process fluids or carriers in polymerization processes.

Figure 2:
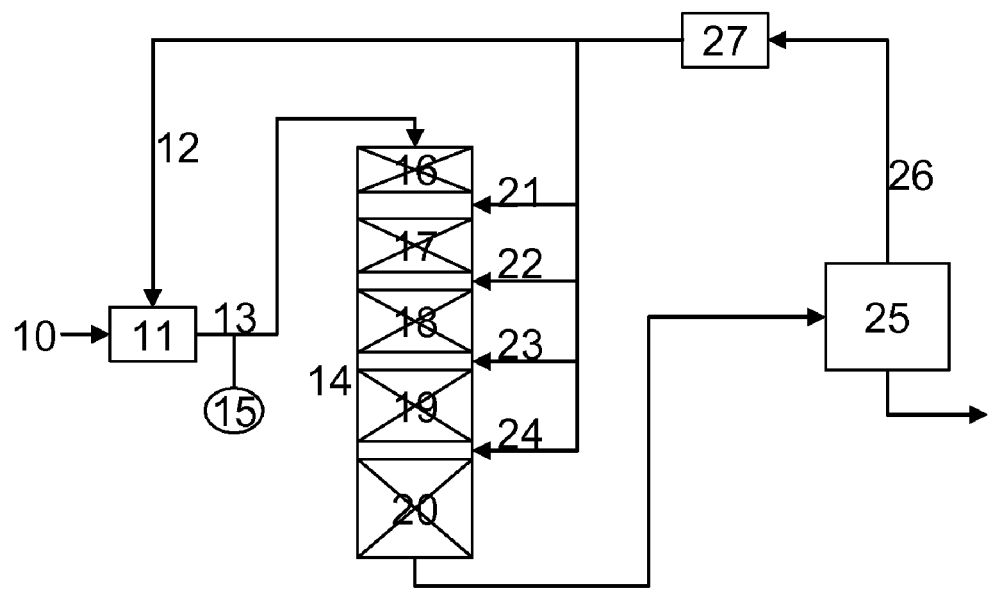
FIG. 2 is a schematic block diagram of an olefin oligomerisation process performed with a chamber reactor in one embodiment of the invention.

The present invention is illustrated by reference to the drawings in which FIG. 1 is a schematic diagram of an olefin oligomerisation process performed with a reactor that may be, according to the present invention, employing the embodiment in which the feed is the byproduct from an MTBE production unit. FIG. 2 is a schematic diagram of an oligomerisation process performed with a chamber reactor.

One embodiment of the process of the present invention is illustrated in the schematic block diagram which is FIG. 1. An olefinic refinery produced feed typically a C4 feed which contains isobutylene and a trace of acetonitrile is first washed in a wash drum to remove the acetonitrile (1). The washed feed then passes to a Unit (2) where the isobutylene is converted to methyl tertiary butyl ether (MTBE) by reaction with methanol. The unreacted C4 materials then pass to a drying step (3) where water and any residual ether is removed. The dry feed then passes along feed pipe (4) to the oligomerisation reactor feed drum (6). An on-line water analyser (5) is provided in feed pipe (4) to check that the feed does not contain more than 30 ppm water, and if necessary adjust the drying conditions.

In the feed drum (6) the fresh feed may be combined with a recycle of diluent and unreacted olefin from the reactor exit and may, if desired, also been combined with the recycle of by products.

The feed having the desired make up is then fed to the oligomerisation reactor (7) which may consist of a series of tubes packed with zeolite catalyst wherein it is oligomerised. The product of oligomerisation is then passed to a stabiliser tower (8) where diluent and unreacted olefin are removed overhead and the overhead may be used for fuel as liquified petroleum gas (LPG) or recycled. The olefin oligomer then passes to a fractionation tower (9) for separation of the olefin oligomer and by products. The by products may be used as feeds for hydroformylation and or recycled.

In the process illustrated in FIG. 2 fresh feed is supplied via line (10) to the feed drum (11) where it is mixed with recycle diluent from line (12). The mixture is then fed via line (13) to the top of the chamber reactor (14) and the water content of the feed is determined by the on-line analyser (15). The chamber reactor consists of five catalyst feeds (16), (17), (18), (19) and (20) and quench streams (21), (22), (23) and (24) are provided between the catalyst beds. Thermocouples (not shown) are also provided between the catalyst beds to determine the bed outlet and preferably also the bed inlet product temperatures, and provide guidance on the required volume of quench fluid. The feed passes down the chamber reactor and passes from the bottom of the reactor to the stabiliser tower or separator (25) where it is separated into oligomer as the heavier product and light unreacted products which pass overhead via line (26) to a condenser (27). The condensed material may then be recycled as diluent, used as the quench fluid or purged.

The present invention involving the drying step and water analysis has been found to result in significant reduction in corrosion in the stabiliser tower. In addition the combination of the removal of acetonitrile and the reduction in the water level has been found to increase catalyst activity which, in turn, has led to a significant increase in catalyst life.

The present invention is further illustrated by reference to the following examples.

Example 1

A refinery butene stream, known as raffinate—2 containing from 60 to 65% n-butenes was oligomerised in a tubular reactor in which the catalyst was ZSM-22. The reaction temperature was maintained between 220 and 240° C. and the inlet pressure of the reactor was 75 barg. The butene conversion to oligomers (octenes) per pass through the reactor was 70 to 90%. In the first run, which was for comparative purposes, the water content of the butene feed stream was 500 ppm and in a second run the water content was reduced to about 10 ppm.

The reduction in the water level resulted in a reduction in the oxygenate level in the reactor effluent from 1100 wt ppm to below 50 wt ppm showing a significant reduction in the presence of species which can cause corrosion in the stabiliser tower.

Example 2

A refinery butene stream containing 90% normal butenes was oligomerised in a tubular reactor containing a bundle of tubes containing ZSM 22 as catalyst. The oligomerisation temperature during the run was between 200 and 300° C., increasing as the run progressed. The reactor inlet pressure was 80 barg and the per pass conversion of butenes was 50 wt %.

Three runs were performed. In the first run, the olefin-containing refinery stream was passed, without a treatment for lowering the level of organic nitrogen-containing Lewis base, and with a hydration treatment to achieve a target water content, to the oligomerisation tubes, and oligomerisation was continued until the temperature had been increased to 300° C. to maintain the target conversion. In the second run, the refinery stream was further subjected to a treatment step to lower the level of organic nitrogen-containing Lewis base prior to oligomerisation by means of a continuous counter-current water wash treatment having 7 theoretical stages, and the treated feed was passed to the oligomerisation reactor. In the third run, the hydration treatment on the feed was discontinued and an existing upstream fractionation step was modified such that the amount of water in the feed to the oligomerisation reactor was reduced as compared to the previous runs.

The olefin-containing feed delivered to the oligomerisation catalyst in the first run contained 3-5 ppm wt of acetonitrile and about 600 ppm by weight of water. The feed delivered to the oligomerisation catalyst in the second run contained between 0.2 and 0.8 ppm wt acetonitrile, with an average of 0.4 ppm wt, and still contained about 600 ppm wt of water. The feed in the third run contained between 0.2 and 0.8 ppm wt acetonitrile, with an average of 0.4 ppm wt, and less than 25 ppm of water. All these concentrations are based on the total hydrocarbon stream.

The catalyst life in tonnes of oligomer produced per tonne of catalyst until the reactor temperature reached 300° C. is shown below.

| Run | Acetonitrile (wt ppm) | Water (wt ppm) | Catalyst life Tonne oligomer/tonne catalyst |
| --- | --- | --- | --- |
| (i) | 3-5 | About 600 | 1000 |
| (ii) | 0.2-0.8 | About 600 | 2500 |
| (iii) | 0.2-0.8 | Less than 25 | 3200 |

This demonstrates that under otherwise equivalent conditions, the process of the invention leads to much improved catalyst life by virtue of less than 30 ppm water in the feed, and also having below 5 ppm of organic nitrogen-containing Lewis base in the feed. Having less than 1 ppm of organic nitrogen-containing Lewis base in the feed gives yet further improved catalyst life.

Furthermore, certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention can be devised without departing from the basic scope thereof, and the scope thereof is determined by the claims that follow.

What is claimed is:

1. A process for the oligomerisation of olefins comprising feeding an olefin-containing feed stream to a reactor containing a molecular sieve oligomerisation catalyst to form a reactor effluent comprising oligomers and unreacted material; wherein the olefin-containing feed stream contains less than 30 ppm wt of water and less than 1 ppm wt of acetonitrile, propionitrile, and mixtures thereof and further comprising feeding the reactor effluent into a stabiliser separator to separate the oligomers and unreacted material and recycling at least partially the unreacted material to the reactor; wherein the at least partially recycled unreacted material also contains less than 30 ppm wt of water.

2. The process according to claim 1 further comprising drying the olefin feed such that it contains less than 30 ppm wt water.

3. The process according to claim 1 further comprising monitoring the water content of the olefin-containing feed stream continuously employing an on line analyser.

4. The process according to claim 1 further comprising providing the reactor with a system adapted for measuring the peak temperature.

5. The process according to claim 4 further comprising providing the reactor with a system adapted for controlling the peak temperature.

6. The process according to claim 5 wherein the system adapted for controlling the peak temperature is a temperature control fluid.

7. The process according to claim 6 wherein the reactor is a tubular reactor comprising a plurality of reactor tubes arranged in a reactor shell.

8. The process according to claim 7 in which the reactor tubes have an internal diameter from 25 to 75 mm, preferably 35 to 50 mm.

9. The process according to claim 7 in which the reactor tubes are arranged substantially vertically and the olefin feed is introduced at the top of the tubes and passes through the tubes in a downward direction.

10. The process according to claim 7 in which a temperature control fluid flows within the reactor shell counter current to the direction of the flow of the olefin feed within the reactor tube.

11. The process according to claim 7 further comprising measuring the peak temperature by means of a multipoint thermocouple disposed in a reaction tube.

12. The process according to claim 7 further comprising controlling the temperature control fluid parameters by means selected from the group consisting of adjusting the temperature, adjusting the pressure and adjusting the flow of said fluid, and combinations thereof, to remove heat from the reactor tubes and maintain the peak temperature in the desired range.

13. The process according to claim 7 further comprising controlling the reactor so that the peak temperature is no more than 50 degrees C. above the temperature of the temperature control fluid as it exits the reactor.

14. The process according to claim 1 in which the reactor comprises a plurality of reaction zones in series.

15. The process in claim 14 further comprising controlling the temperature by injecting a quenching fluid into the process fluid between the reaction zones.

16. The process of claim 15 further comprising controlling the temperature so that the temperature increase across a reaction zone is no more than 50 degrees C.

17. The process according to claim 5 further comprising maintaining the peak temperature below 260 degrees C.

18. The process according to claim 1 in which the olefin feed is selected from the group consisting of an olefin feed containing up to 65 wt % propylene and an olefin feed containing up to 80 wt % butene.

19. The process according to claim 1 in which the reactor product is exiting the reactor at a pressure in the range 60 to 80 barg.

20. The process according to claim 1 further comprising operating the process at an olefin feed stream space velocity of from 1-15 w/w/h.

21. The process according to claim 1 in which the temperature of the feed entering the reactor is in the range of from 150 to 250 degrees C.

22. The process according to claim 1 further comprising contacting the feed with the catalyst at a temperature in the range of from 150 to 300 degrees C.

23. The process according to claim 1 wherein the olefin conversion per pass is in the range of from 40 to 80%.

* * * * *